United States Patent
Stapleton et al.

(10) Patent No.: US 9,696,259 B2
(45) Date of Patent: Jul. 4, 2017

(54) OPTODE SENSOR WITH INTEGRATED REFERENCE

(71) Applicant: LumaSense Technologies Holdings, Inc., Santa Clara, CA (US)

(72) Inventors: Terry M. Stapleton, Santa Clara, CA (US); Gregor Hsiao, Santa Clara, CA (US); John Paul Jeffrey, Santa Clara, CA (US)

(73) Assignee: LumaSense Technologies Holdings, Inc., Santa Clara, CA (US)

( * ) Notice: Subject to any disclaimer, the term of this patent is extended or adjusted under 35 U.S.C. 154(b) by 9 days.

(21) Appl. No.: 14/829,355

(22) Filed: Aug. 18, 2015

(65) Prior Publication Data
US 2017/0052117 A1 Feb. 23, 2017

(51) Int. Cl.
*H01J 65/08* (2006.01)
*G01N 21/64* (2006.01)

(52) U.S. Cl.
CPC ... *G01N 21/643* (2013.01); *G01N 2021/6434* (2013.01); *G01N 2201/061* (2013.01); *G01N 2201/121* (2013.01)

(58) Field of Classification Search
CPC ......... G01N 21/8483; G01N 33/54346; G01N 21/6428; G01N 21/648; G01N 21/783;
(Continued)

(56) References Cited

U.S. PATENT DOCUMENTS 6,360,585 B1 * 3/2002 Potyrailo ............. G01N 29/036
422/83
8,323,982 B2 * 12/2012 LeBoeuf .............. G01N 27/305
204/157.15
(Continued)

FOREIGN PATENT DOCUMENTS

EP 2620764 A1 7/2013

OTHER PUBLICATIONS

International Search Report issued in corresponding International Application No. PCT/US2016/047520 dated Nov. 14, 2016 (5 pages).
(Continued)

*Primary Examiner* — David J Makiya
*Assistant Examiner* — Taeho Jo
(74) *Attorney, Agent, or Firm* — Osha Liang LLP (57) ABSTRACT

A system for obtaining a measurement of a species of interest. The system includes one or more reference regions, a sensor region, an exciter unit, a detector unit and a processing unit. The exciter unit exposes first and second chemical transducers in the reference and sensor regions, respectively, to an excitation light while they are exposed to reference environments and an analyte, respectively. The detector unit measures responses of the first and the second chemical transducers to the excitation light. The processing unit determines a compensation for aging of the first chemical transducer from a discrepancy between the measurements of the responses of the first chemical transducer and reference responses. The processing unit applies the compensation for aging to the measurement of the response of the second chemical transducer to obtain the measurement of the species of interest in the analyte.

20 Claims, 5 Drawing Sheets

(58) Field of Classification Search
CPC ....... G01N 2201/062; G01N 2201/061; G01N 2201/121; G01N 2291/021; G01N 2333/904
USPC ...................................................... 250/459.1
See application file for complete search history.

(56) References Cited

U.S. PATENT DOCUMENTS

| | | | |
|---|---|---|---|
| 2004/0058385 A1 | 3/2004 | Abel et al. | |
| 2004/0245470 A1* | 12/2004 | Nadezhdinskii | G01N 21/39 250/343 |
| 2005/0158850 A1* | 7/2005 | Kubo | G01N 21/553 435/287.2 |
| 2006/0177889 A1* | 8/2006 | Anvar | C12Q 1/26 435/25 |
| 2006/0256676 A1* | 11/2006 | Nolte | G01N 33/54373 369/47.1 |
| 2007/0220978 A1* | 9/2007 | Su | G01N 29/0681 73/632 |
| 2009/0156917 A1* | 6/2009 | Martini | A61B 5/14532 600/341 |
| 2010/0086933 A1* | 4/2010 | Hospach | G01N 21/77 435/6.11 |
| 2010/0141952 A1* | 6/2010 | Myrick | G01J 3/02 356/451 |
| 2011/0105867 A1 | 5/2011 | Schultz et al. | |
| 2011/0153259 A1* | 6/2011 | Michael | G01N 27/286 702/123 |
| 2011/0275985 A1* | 11/2011 | Lowery, Jr. | A61B 5/14865 604/66 |
| 2012/0285224 A1* | 11/2012 | Zachmann | G01N 35/1097 73/64.56 |
| 2013/0217003 A1* | 8/2013 | Hanko | G01N 33/54306 435/5 |
| 2013/0323858 A1 | 12/2013 | Abdulhalim | |
| 2014/0165704 A1* | 6/2014 | Maity | G01N 25/005 73/25.01 |
| 2014/0271366 A1* | 9/2014 | Denomme | G01N 21/554 422/69 |
| 2015/0232913 A1* | 8/2015 | Reardon | C12Q 1/005 435/14 |
| 2015/0299881 A1* | 10/2015 | Kim | G02B 1/005 204/478 |

OTHER PUBLICATIONS

Written Opinion issued in corresponding International Application No. PCT/US2016/047520 dated Nov. 14, 2016 (7 pages).

* cited by examiner

OPTODE SENSOR WITH INTEGRATED REFERENCE

BACKGROUND

An optode sensor may optically determine the presence and/or concentration of one or more species of interest in an environment, based on a response of a chemical transducer. The chemical transducer may age over time.

SUMMARY

In general, in one aspect, the invention relates to a system for obtaining a measurement of a species of interest in an analyte. The system includes one or more reference regions including a first chemical transducer, a sensor region including a second chemical transducer, an exciter unit, a detector unit and a processing unit. The one or more reference regions are exposed to one or more reference environments including one or more reference concentrations of the species of interest. The sensor region is exposed to the analyte. The exciter unit is used for exposing the first chemical transducer in the one or more reference regions to an excitation light while the first chemical transducer in the one or more reference regions is exposed to the one or more reference environments. The exciter unit is further used for exposing the second chemical transducer in the sensor region to the excitation light while the second chemical transducer in the sensor region is exposed to the analyte. The detector unit is used for obtaining a measurement of one or more responses of the first chemical transducer in the one or more reference regions to the excitation light, and for obtaining a measurement of a response of the second chemical transducer in the sensor region to the excitation light. The processing unit is used for determining a compensation for aging of the first chemical transducer in the one or more reference regions from a discrepancy between the measurement of the one or more responses of the first chemical transducer to the excitation light and one or more reference responses of the first chemical transducer. The processing unit is further used for obtaining the measurement of the species of interest in the analyte by applying the compensation for aging of the first chemical transducer to the measurement of the response of the second chemical transducer.

In general, in one aspect, the invention relates to a method for obtaining a measurement of a species of interest in an analyte using an optode sensor. The method includes exposing one or more reference regions that include a first chemical transducer to one or more reference environments that include one or more reference concentrations of the species of interest. The method further includes exposing the first chemical transducer in the one or more reference regions to excitation light and obtaining a measurement of one or more responses of the first chemical transducer in the one or more reference regions to the excitation light during the exposure to the one or more reference environments. The method also includes determining a compensation for aging of the first chemical transducer from a discrepancy between the measurement of the one or more responses of the first chemical transducer in the one or more reference regions to the excitation light and one or more reference responses of the first chemical transducer. In addition, the method includes exposing a sensor region that includes a second chemical transducer to the analyte and exposing the second chemical transducer in the sensor region to excitation light, and obtaining a measurement of a response of the second chemical transducer in the sensor region to the excitation light during the exposure to the analyte. The method also includes obtaining the measurement of the species of interest in the analyte by applying the compensation for aging of the first chemical transducer to the measurement of the response of the second chemical transducer to the excitation light during the exposure to the analyte.

Other aspects of the invention will be apparent from the following description and the appended claims.

DETAILED DESCRIPTION

Specific embodiments of the invention will now be described in detail with reference to the accompanying figures. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In the following description of FIGS. 1-5, any component described with regard to a figure, in various embodiments of the invention, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments of the invention, any description of the components of a figure is to be interpreted as an optional embodiment, which may be implemented in addition to, in conjunction with, or in place of the embodiments described with regard to a corresponding like-named component in any other figure.

In general, embodiments of the invention relate to optode sensors with an integrated reference, and methods for taking measurements, using the optode sensor with integrated reference, and for calibrating the optode sensor with integrated reference. More specifically, embodiments of the invention relate to optode sensors that may measure the presence and/or concentration of one or more species of interest in an analyte, e.g., in a gas or a liquid environment, using a photochemical process of a chemical transducer, and where the measurements obtained from the chemical transducer are processed in accordance with one or more embodiments of the invention, in order to compensate for a change in the sensitivity of the optode sensor, caused by aging of the chemical transducer.

Figure 1:
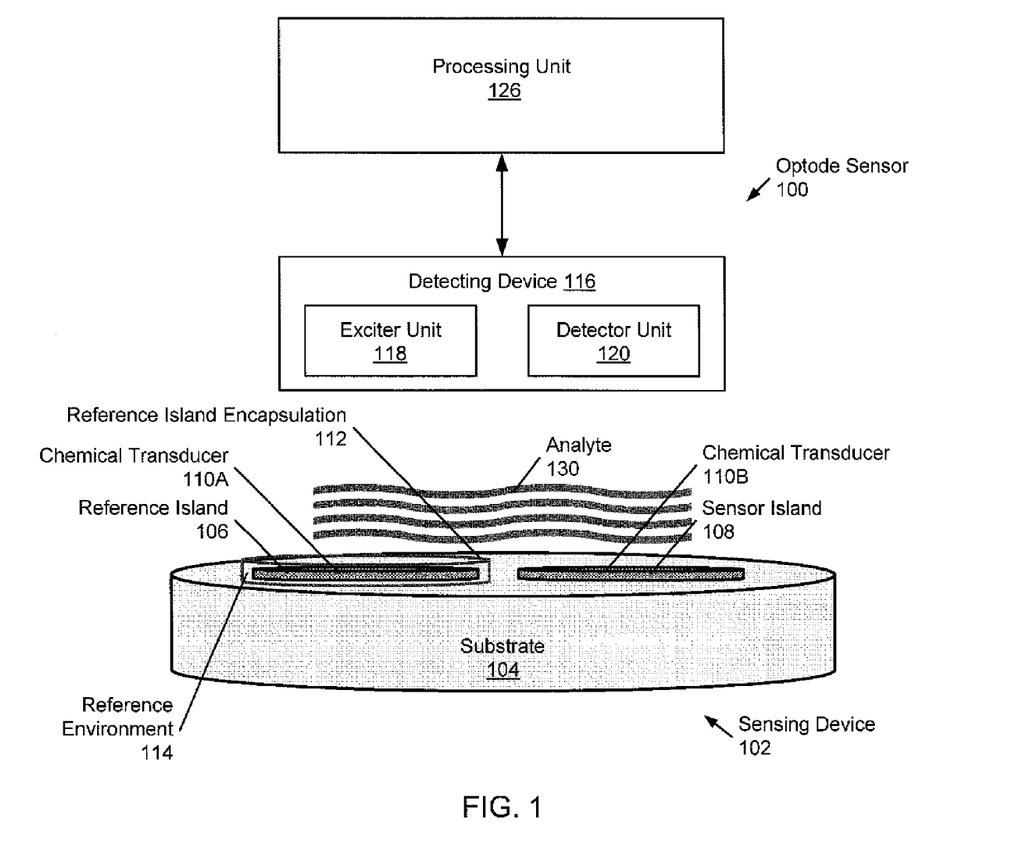
FIG. 1 shows a schematic diagram of an optode sensor with integrated reference, in accordance with one or more embodiments of the invention.

FIG. 1 shows a schematic view of an optode sensor with integrated reference, in accordance with one or more embodiments of the invention. The optode sensor (100) may be used to determine presence and/or concentration of a species of interest in an analyte (130). The optode sensor (100) may include a sensing device (102) and a detecting device (116). In one or more embodiments of the invention, elements of the sensing device, including at least the sensor island (108), are exposed to the analyte (130). The sensor island (108), in accordance with one or more embodiments of the invention, accommodates a chemical transducer (110.B) that is sensitive to the species of interest and may undergo a change, depending on the presence and/or concentration of the species of interest in the analyte (130). In one or more embodiments of the invention, the detection device (116) is used to assess the change of the chemical transducer (110.B) in response to being exposed to the analyte (130), and further to obtain a reference response by measuring a response of a chemical transducer (110.A), accommodated by a reference island (106), that is not exposed to the analyte (130). The measurements of the responses of the chemical transducers (110.A and 110.B), obtained by the detection device (116), may be used to determine the presence and/or concentration of the species of interest in the analyte (130). The detecting device (116) may interface with a processing unit (126) that may execute at least some of the steps of the methods used to determine the presence and/or concentration of the species of interest, as described in detail below, with reference to FIGS. 3 and 4.

The sensing device (102) in accordance with one or more embodiments of the invention includes a substrate (104). The substrate may be formed from materials that are impermeable to the species of interest. The substrate may be, for example, formed from a polymer, metal, silicone, inorganic oxides such as quartz, etc. In the exemplary embodiment, shown in FIG. 1, the substrate (104) accommodates the sensor island (108) and the reference island (106). In alternative embodiments, the substrate (104) may accommodate any number of reference islands (106) and sensor islands (108), e.g., in the form of a grid of sensor and/or reference islands. In an alternative embodiment, the reference island (106) and the sensor island (108) may be separated, i.e., separate substrates (104) may be used to accommodate the reference island (106) and the sensor island (108). The sensor island (108), in accordance with one or more embodiments of the invention, is a sensing layer that includes a chemical transducer (110.B) that undergoes a change depending on the presence and/or concentration of a species of interest in the environment (i.e., the analyte (130)) surrounding the sensor island (108). More specifically, the chemical transducer (110.B) may change its optical characteristics, such as, for example, its fluorescence or phosphorescence characteristics, as further described in detail below. The chemical transducer (110.B) may be directly deposited on the surface of the substrate (104) as an island (108) of arbitrary size and/or shape, it may be housed by a cavity in the substrate, it may be dispersed or dissolved in a support matrix (e.g., a polymer that is permeable to the species of interest), etc. Those skilled in the art will appreciate that the invention is not limited to the aforementioned examples for accommodating the chemical transducer on the substrate. Any type of accommodation of the chemical transducer on the substrate that is chemically compatible with the surrounding environment, i.e., the analyte (130), and that enables the species of interest to reach the chemical transducer may be employed.

Analogous to the sensor island (108), the reference island (106), in accordance with one or more embodiments of the invention, is a sensing layer that includes a chemical transducer (110.A) that undergoes a change depending on the presence and/or concentration of a species of interest in the environment surrounding the reference island (106). In one or more embodiments of the invention, the reference island (106) accommodating the chemical transducer (110.A) is substantially similar to the sensor island (108) accommodating the chemical transducer (110.B). Structural and/or functional differences between the sensor island (108) and the reference island (106), including the chemical transducers (110.A and 110.B), if they exist, may be explicitly considered and addressed by the methods described below with reference to FIGS. 3 and 4. In the exemplary embodiment shown in FIG. 1, the reference island (106), unlike the sensor island (108), is enclosed by a reference island encapsulation (112). The reference island encapsulation (112) may isolate the reference island (106) and the chemical transducer (110.A) from the analyte (130) and the species of interest that the analyte may contain. Further, the reference island encapsulation (112) encloses a reference environment (114), thereby exposing the chemical transducer (110.A) of the reference island (106) to the reference environment (114).

In one or more embodiments of the invention, the reference environment (114) contains the species of interest in a known, fixed reference concentration. When an analyte (130) is analyzed for a species of interest, measurements obtained from the chemical transducer (110.B) of the sensor island (108) are compared to measurements obtained from the chemical transducer (110.A) of the reference island (106), in accordance with one or more embodiments of the invention, as described in detail below with reference to FIGS. 3 and 4. The reference concentration of the species of interest in the reference environment (114) may be chosen to approximately match the expected concentration of the species of interest to be measured in the analyte (130), e.g., if high concentrations of the species of interest are expected in the analyte (130), the reference environment (114) may also contain a high concentration of the species of interest, and alternatively if low concentrations of the species of interest are expected in the analyte (130), the reference environment (114) may also containing a low concentration of the species of interest. In one embodiment of the invention, multiple reference islands (106) with reference environments (114) containing different concentrations of the species of interest may be used to cover a wide range of concentrations of the species of interest.

In order to maintain the reference environment (114) with a known, fixed concentration of the species of interest, the encapsulation (112) is therefore formed from a material that is impermeable to the species of interest. The material used for the encapsulation (112) may be, for example, a polymer that is impermeable to the species of interest. The encapsulation (112) may further be optically transparent (i.e., highly optically transmissive) for the wavelengths being used by the detecting device (116) to read the sensing device (102), as further described below.

Due to the encapsulation (112) that encloses the sensor island (108), the reference island (106) and the sensor island (108) are therefore exposed to different environments (the reference island (106) being exposed to the reference environment (114) and the sensor island (108) being exposed to the analyte (130). In one or more embodiments of the invention, the reference island (106) and the sensor island (108) are however both exposed to otherwise similar conditions, e.g., the reference island (106) and the sensor island (108) may be equally affected by light, temperature, etc.

In one or more embodiments of the invention, the chemical transducers (110.A and 110.B) of the reference island (106) and the sensor island (108) may be, for example, a fluorophore or a phosphor, i.e., a fluorescent or phosphorescent chemical compound capable of re-emitting light upon exposure to excitation light. The frequency of the re-emitted light, may be different from the frequency of the excitation light. The characteristics of the re-emitted light, in accordance with one or more embodiments of the invention, may depend on the presence and/or concentration of the species of interest, i.e., the chemical transducers (110.A and 110.B) may change their optical characteristics in response to being exposed to a species of interest. The species of interest may, for example, cause luminescence quenching, i.e., in the example of a fluorophore or a phosphor being used as a chemical transducer, the fluorescence or phosphorescence response may be weakened in the presence of the species of interest. In one embodiment of the invention, the chemical transducers (110.A and 110.B) are sensitive to the presence of oxygen, i.e., they change their optical characteristics in response to being exposed to oxygen. Examples for chemical transducers that change their optical characteristics in response to an exposure to oxygen are polycyclic aromatic hydrocarbons and porphyrins such as pyrenebutyric acid, perylene dibutyrate, pyrene/perylene, 9,10-diphenylanthracene, decacylen and tetraphenylporphyrin and metalorganic complexes including ruthenium(II) complexes, platinum(II) complexes or porphyrins, palladium(II) porphyrins, rhenium (I) complexes, osmium(II) complexes, gold(I) complexes, lead(II) complexes, aluminum(III) complexes. In an alternative embodiment of the invention, the chemical transducers (110.A and 110.B) are sensitive to the presence of ammonia. An example for a chemical transducer that changes its optical characteristics in response to an exposure to ammonia is zinc tetraphenylporphyrin. Other chemical transducers may change their optical characteristics, for example, in the presence of hydrazine, nitric oxide, etc. Those skilled in the art will appreciate that the invention is not limited to the aforementioned species of interest, chemical transducers, and changes of optical characteristics. Rather, any species of interest may be detected by any type of chemical transducer that responds to the presence of the species of interest with any type of detectable change in its optical characteristics.

In one or more embodiments of the invention, the response of the chemical transducers (110.A and 110.B) to the species of interest may decrease over time. In case of the chemical transducers (110.A and 110.B) being fluorophores or phosphors, the intensity and the time constant of the fluorescence or phosphorescence response, respectively, may decrease as a result of photo-bleaching, where a photochemical alteration of the fluorophore or phosphor molecules may, over time, render the fluorophore or phosphor molecules unable to fluoresce or phosphoresce. In one or more embodiments of the invention, the chemical transducer (110.A) of the reference island (106) and the chemical transducer (110.B) of the sensor island (108) are exposed to substantially the same light (wavelength, intensity, duration of exposure). Specifically, the exposure to excitation light, provided by the detecting device (116) as described in detail below, may be similar. Further the exposure to ambient light may be similar. Accordingly, in accordance with one or more embodiments of the invention, the chemical transducer (110.A) of the reference island (106) and the chemical transducer (110.B) of the sensor island (108) are similarly affected by photo-bleaching.

Continuing with the discussion of the embodiment shown in FIG. 1, the optode sensor (100) includes a detecting device (116). The detecting device (116) may be optical instrumentation suitable for causing and detecting optical responses of the chemical transducers (110.A and 110.B) of the reference island (106) and the sensor island (108). The detecting device (116) may be separate from the sensing device and may or may not be exposed to the analyte (130). The detecting device (116) may include an exciter unit (118) and a detector unit (120). The exciter unit (118) may be a light source, used to provide an excitation light to the chemical transducers (110.A and 110.B) during a measurement of the analyte (130). The detector unit (120) may be a light sensing device, used to capture and measure light re-emitted by the chemical transducers (110.A and 110.B) in response to the excitation light. Because the characteristics of the re-emitted light depend on the presence and/or concentration of the species of interest, the measurements of the re-emitted light, obtained by the detector unit (120), may be used to determine presence and/or concentration of the species of interest. A detailed description of the detector device (116) is provided below, with reference to FIG. 2. Further, a detailed description of the methods used for determining the presence and/or concentration of the species of interest is provided below, with reference to FIGS. 3 and 4.

In one or more embodiments of the invention, the detecting device (116) may interface with the processing unit (126) executing at least some of the steps of the methods used to determine the presence and/or concentration of the species of interest. The processing unit (126) may be, for example, a mobile device (e.g., a laptop computer, smart phone, personal digital assistant, tablet computer, or other mobile device), a desktop computer, server, a blade in a server chassis, or any other type of computing device or devices that includes at least the minimum processing power, memory, and input and output device(s) to perform one or more embodiments of the invention. In one embodiment of the invention, the processing unit (126) may form a single unit with the optode sensor (100). For example, the processing unit and the optode sensor may be housed in a probe. The processing unit may further be integrated with the detecting device (116) on a single printed circuit board. The processing unit (126) may include one or more computer processor(s), associated memory (e.g., random access memory (RAM), cache memory, flash memory, etc.), one or more storage device(s) (e.g., a hard disk, an optical drive such as a compact disk (CD) drive or digital versatile disk (DVD) drive, a flash memory stick, etc.), and numerous other elements and functionalities, such as input and output device enabling a user to interact with the processing unit. The processing unit (126) may further be connected to a network (e.g., a company's local area network (LAN), a wide area network (WAN) such as the Internet, mobile networks, or any other type of network via a network interface connection. In one embodiment of the invention, the processing unit (126) further includes a communication interface for communicating with the detecting device (116). The communication with the detecting device may include sending control commands to the exciter unit (118) and receiving data from the detector unit (120). Depending on the connectivity of the detecting device (116), the communication interface may include a digital interface, such as USB, RS232, etc. and/or a an analog interface, for example via analog-to-digital and digital-to-analog converters.

Figure 2:
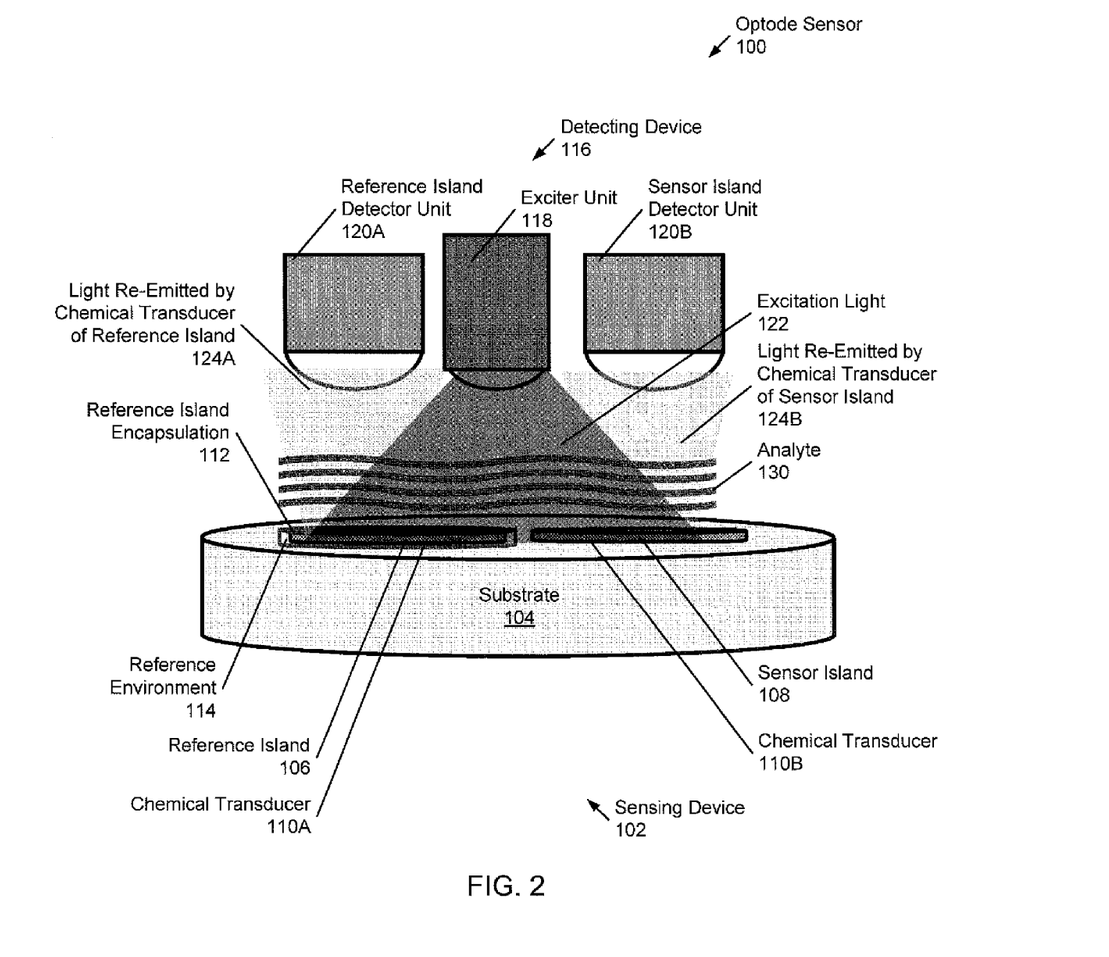
FIG. 2 shows an optode sensor with integrated reference in accordance with one or more embodiments of the invention.

FIG. 2 shows an exemplary embodiment of an optode sensor with integrated reference, in accordance with one or more embodiments of the invention. The optode sensor with integrated reference may include a sensing device (102) and a detecting device (116). The sensing device (102) may be similar to the sensing device described above, with reference to FIG. 1. In the exemplary embodiment shown in FIG. 2, the detecting device includes an exciter unit (118) and two detector units (120A and 120B). The exciter unit (118) is a device suitable for exposing the chemical transducers (110A and 110B) of the reference and sensor islands (106 and 108) to an excitation light (122) that may cause the chemical transducers (110A and 110B) to respond with the re-emission of light (124A and 124B), as further described in detail below.

The exciter unit (118) may be, a light source, e.g. a lamp, an LED, a laser, etc, capable of causing the chemical transducers (110A and 110B) to respond by re-emitting light. The excitation light (122) provided by the exciter unit (118) may be, for example of a particular wavelength, intensity, polarity, and may be provided for a particular duration, etc., as determined by the chemical transducers (110A and 110B). For example, the exciter unit may be based on a blue LED in embodiments where the chemical transducers (110A and 110B) include ruthenium complexes. In one or more embodiments of the invention, the exposure of the chemical transducer (110A) of the reference island (106) and the chemical transducer (110B) of the sensor island (108) to the excitation light (122) provided by the exciter unit (118) is substantially the same, thus resulting in similar aging, i.e., photo-bleaching, of the chemical transducers (110A and 110B) over time. In the exemplary embodiment shown in FIG. 2, the exciter unit (118) simultaneously provides excitation light (122) to the chemical transducer (110A) of the reference island (106) and to the chemical transducer (110B) of the sensor island (108). The exciter unit (118), in the embodiment shown in FIG. 2 is located equidistantly between the reference island (106) and the sensor island (108), thereby exposing the chemical transducers (110A and 110B) of the reference and sensor islands (106 and 108) to equal amounts of excitation light (122). In an alternative embodiment of the invention, a rotating focus lens and/or mirror is/are used to sequentially or simultaneously provide excitation light (122) to the chemical transducers (110A and 110B) of the reference and the sensor islands (106 and 108). In yet another embodiment of the invention, the exciter unit (118) may include separate light sources (e.g., one LED targeting the reference island and one LED targeting the sensor island) to provide equal amounts of excitation light to the reference and sensor islands. The excitation light (122) emitted by the exciter unit(s) (118) may be pulsed or continuous.

Continuing with the discussion of the exemplary embodiment shown in FIG. 2, the detecting device (116) includes two detector units (120A, 120B). The detector units (120A, 120B) may be any type of detectors suitable for the detection of light re-emitted by the chemical transducers (110A, 110B) of the reference and the sensor islands (106, 108), e.g. the detectors may be photodiodes, phototransistors, photoresistors, CCD arrays, CMOS arrays, etc. The output signal of the detector units (120A, 120B) may signal the amount of light that is re-emitted by the chemical transducers (110A, 110B) of the reference and sensor islands (106, 108). The output signal may be, for example, a voltage, a current, or a digital signal that may be linearly or nonlinearly related to the amount of light re-emitted by the chemical transducers (110A, 110B) of the reference and sensor islands (106, 108). In the exemplary embodiment shown in FIG. 2, one detector unit (120A) receives light re-emitted by the chemical transducer (110A) of the reference island (106), and one detector unit (120B) receives light re-emitted by the chemical transducer (110B) of the sensor island (108). In an alternative embodiment of the invention, a single detector unit (120) may be used to capture re-emitted light from both the reference and sensor islands. For example, a rotating focus lens and/or mirror may be used to sequentially capture light (124A, 124B) re-emitted by the chemical transducers (110A, 110B) of the reference and the sensor islands (106 and 108) by the single detector unit (120).

In one embodiment of the invention, the exciter unit (118) and the detector unit (120) may use an identical pathway for providing the excitation light by the exciter unit (118) and for receiving the re-emitted light by the detector unit (120). For example, a rotating focus lens and/or mirror may be used to alternate between interrogating reference and sensor islands (106, 108) arranged about a fixed radius from the center of the lens and/or mirror. The position of the rotating lens and/or mirror may be time dependent, and timing information may therefore be used to determine which island is being interrogated.

In one or more embodiments of the invention, the exposure of the chemical transducers (110A, 110B) of the reference and sensor islands (106, 108), the sensitivity of the detector units (120) receiving the re-emitted light (124A, 124B) and the attenuation of excitation light (122) and re-emitted light (124A, 124B) along the entire optical pathway from exciter unit (118) to detector unit (120) are substantially the same. If differences exist, they may be explicitly considered and addressed by the methods described below. For example, if the reference island encapsulation (114) attenuates the excitation light and/or the re-emitted light, a calibration may be performed to determine the degree of attenuation, thus allowing correction for the attenuation.

Continuing with the discussion of the optode sensor with integrated reference, in one or more embodiments of the invention, components of the optode sensor with integrated reference (100) are integrated in a body suitable to hold and seal them, as necessary. Depending on the intended use of the optode sensor (100) the structure of the body may vary. For example, in cases where gaseous analytes are analyzed, the detecting device (116) may not require a protection against fluids, whereas liquid analytes may require fluid-tight sealing of the detecting device (116). In one embodiment of the invention, both the sensing device (102) and the detecting device (116) may be exposed to the analyte (130). Accordingly, the sensing device (102) and the detecting device (116) may form a single unit. In an alternative embodiment, only the sensing device (102) may be exposed to the analyte, for example by placing the sensing device (102) into a container holding the analyte (130), while operating the detecting device (116) outside of the container. Measurements may be performed, across transparent walls of the container. In yet another embodiment of the invention, where the reference island is separate and independent from the sensor island, the optode sensor with the integrated reference may include two separate bodies, both equipped with detecting devices for interrogating the chemical transducers (110A, 110B) of reference and sensor islands (106, 108).

One skilled in the art will recognize that the structure of the optode sensor with integrated reference (100) is not limited to the components shown in FIGS. 1 and 2. For example, the optode sensor may include any number of reference islands and sensor islands, ranging from a single reference island and a single sensor island to arrays of sensor and reference islands. Multiple reference islands may be used, for example, to rely on multiple concentrations of the species of interest as references. Multiple sensor and reference islands may in addition be used, for example, to sense different species of interest. Further, the design of the reference and sensor islands, including size, shape and materials, may vary. Different analytes may, for example, require different materials, e.g. most materials may be compatible with air, whereas fewer materials may be compatible with oil, acids, etc. The sensor and reference island (s) may be located on the same substrate, or they may be separately located. In multiple embodiments the invention may be based on different designs of the detecting device. The detecting device may include a single light source, or separate light sources, e.g. one light source per reference and/or sensor island. In case of an array of sensor and/or reference islands, an array of light sources may be used. The light sources may be of any type capable of providing excitation light that is compatible with the chemical transducer, i.e., excitation light that causes the chemical transducer to re-emit light. The light sources may be monochromatic or they may provide a spectrum of wavelengths that may be visible and/or invisible (including, e.g., infrared and ultraviolet light). The light sources may be, for example, LEDs, lasers, incandescent, fluorescent and high-intensity discharge light bulbs. Further, any number of detector units of any type suitable for detecting light re-emitted by the reference and sensor island(s) may be used. For example, a detector unit may be a photo resistor, a photo diode, a photo transistor, a CCD array, a CMOS array, etc. In addition, as previously discussed, different types of chemical transducers or combinations of chemical transducers may be used. A chemical transducer may be used for detecting a single species of interest or multiple species of interest. Although in the embodiment shown in FIGS. 1 and 2, the exciter and detector units are co-located on one side of the sensing device, exciter and detector units may be located on opposite sides of the sensing device. In such an embodiment, the sensing device, including the substrate, would be optically transparent or semi-transparent. The substrate may be covered with an array of sensor and/or reference islands, with an exciter unit providing excitation light from one side of the sensing device, and a detector unit, located on the opposite side, capturing the re-emitted light of the array of sensor islands. The response of the array of sensor and/or reference islands may be captured, for example, by a CCD array. A pixel or a set of adjacent pixels of the CCD array may receive light re-emitted by a particular sensor or reference island only. Alternatively, a fiber array, aligned with the array of sensor and/or reference islands may be used to capture the responses of the sensor and/or reference islands. Additional optical components such as lenses and mirrors may be used to match the geometry of the array of sensor and/or reference islands with the geometry of detecting device.

Figure 3:
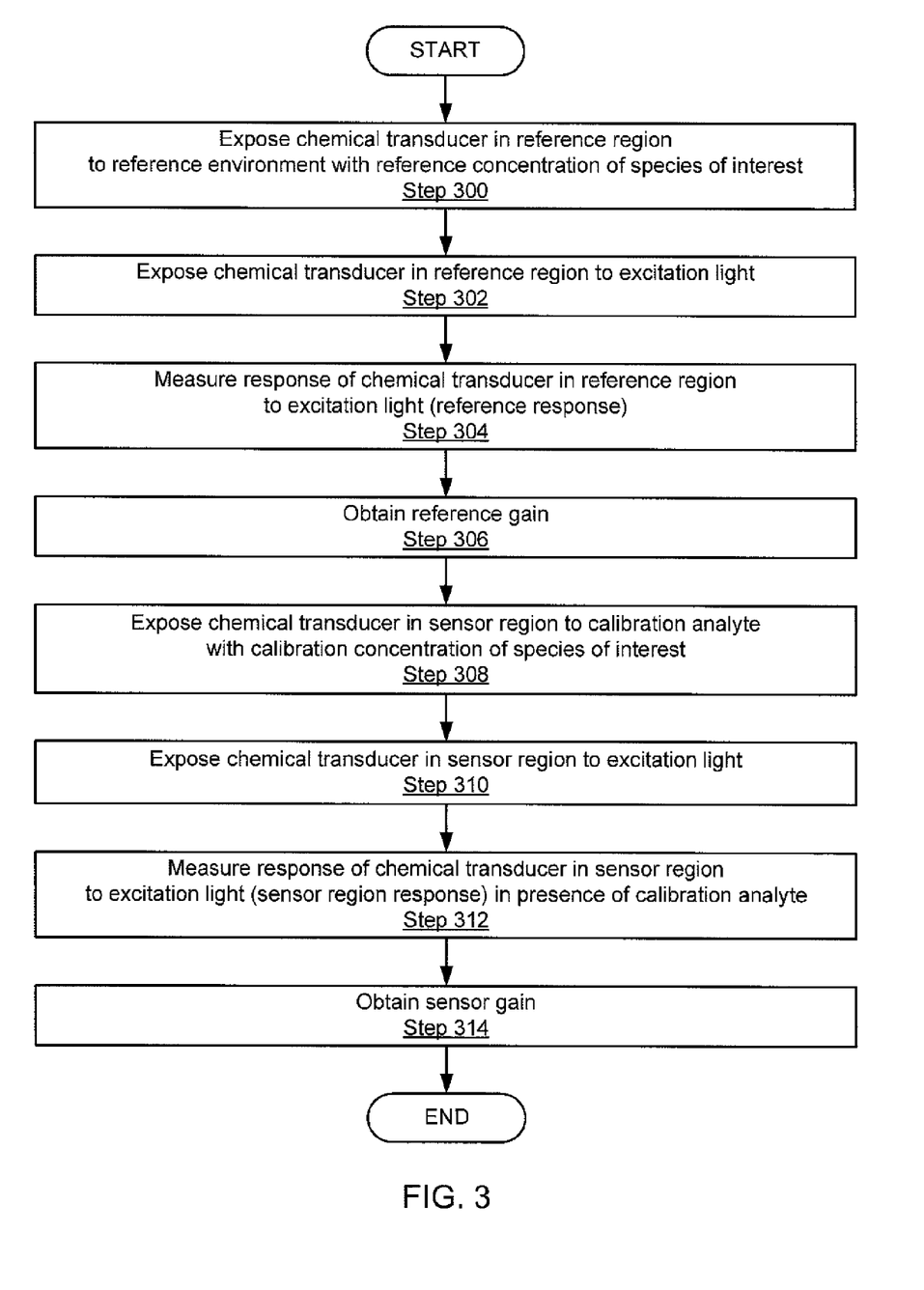
FIG. 3 shows a flowchart in accordance with one or more embodiments of the invention.
Figure 4:
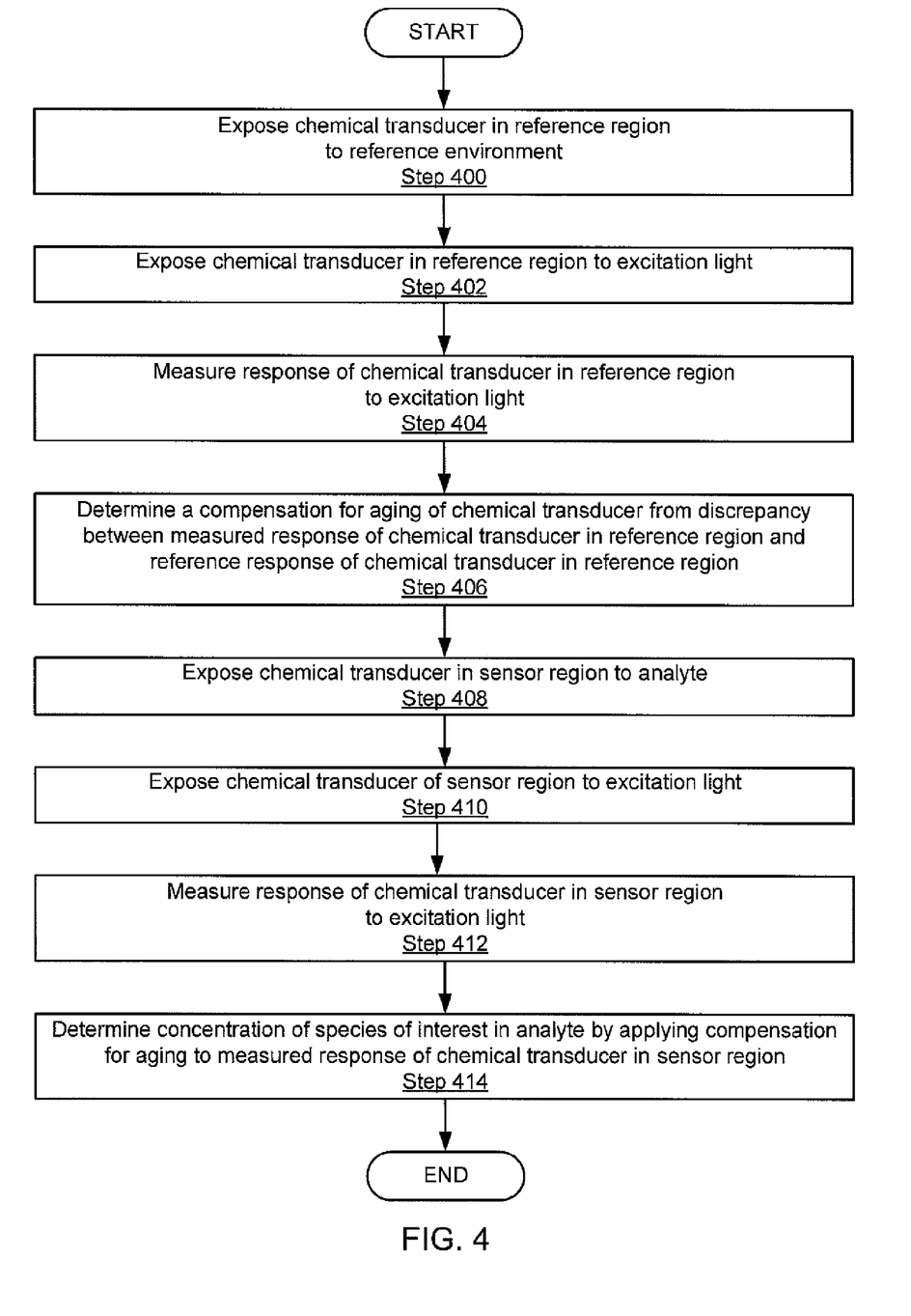
FIG. 4, shows a flowchart in accordance with one or more embodiments of the invention.

FIGS. 3 and 4 show flowcharts in accordance with one or more embodiments of the invention.

While the various steps in the flowcharts are presented and described sequentially, one of ordinary skill will appreciate that some or all of these steps may be executed in different orders, may be combined or omitted, and some or all of the steps may be executed in parallel. In one embodiment of the invention, the steps shown in FIGS. 3 and 4 may be performed in parallel with any other steps shown in FIGS. 3 and 4 without departing from the invention.

FIG. 3 shows a method for performing an initial calibration of an optode sensor with integrated reference, in accordance with one or more embodiments of the invention. The initial calibration may be performed prior to the first use of the optode sensor, for example as a step of the manufacturing process. The initial calibration may be performed to determine the sensing characteristics of the optode sensor with integrated reference. The initial calibration may therefore allow for compensation of manufacturing tolerances such as differences in exciter unit performance (e.g. deviations in the brightness of the emitted excitation light), chemical transducer performance (e.g. deviations in the amount of chemical transducer deposited on sensing and reference islands), detector unit performance (e.g. deviations in the sensitivity to light re-emitted by the chemical transducers), optical misalignments, etc. More specifically, the initial calibration may be performed (i) to identify a relationship between the known concentration of the species of interest in the reference region (i.e., the reference environment) and the reference island detector unit signal, and (ii) to identify a relationship between the known concentration of the species of interest in a calibration analyte in the sensor region (i.e., the region surrounding the sensor island) and the sensor island detector unit signals. The identified characteristics may be for example, gain factors or response curves that relate the known calibration and reference concentrations to the output signals of the detector unit(s) The identified characteristics may later be used, in accordance with one or more embodiments of the invention, to estimate a concentration of a species of interest in an analyte, based on the output signals of the sensor and reference island detector units obtained when measuring a species of interest in an analyte, as described in detail below with reference to FIG. 4. In one embodiment of the invention the calibration may only need to be performed once, e.g. after final assembly of the optode sensor with integrated reference. The calibration may not need to be performed immediately prior to performing a measurement.

Turning to FIG. 3, in Step 300, the chemical transducer in the reference region (e.g., a reference island on a substrate, as shown in FIGS. 1 and 2) is exposed to the reference environment that contains a reference concentration of the species of interest. The reference concentration may be known and defined. In one embodiment of the invention, the reference region may be a reference island that accommodates the chemical transducer. The reference island may be enclosed by a reference island encapsulation that holds the reference environment with the known defined reference concentration of the species of interest. The transducer in the reference region may therefore be permanently exposed to the reference environment with the known, defined reference concentration of the species of interest. The reference concentration of the species of interest may be chosen to approximately match the concentrations of the species of interest to be measured by the optode sensor with integrated reference. For example, a reference environment with a 0% reference concentration of the species of interest may be chosen if the optode sensor with integrated reference is intended to measure analytes that contain low concentrations of the species of interest.

In Step 302, the chemical transducer in the reference region is exposed to excitation light. The excitation light may be provided by the exciter unit of the detecting device. The duration of the exposure to the excitation light may vary, for example the exposure may be pulsed, or it may be continuous. The characteristics of the excitation light (including intensity, wavelength and duration of exposure) may be selected such that the chemical transducer may, in response, re-emit light, for example via fluorescence or phosphorescence, as previously described.

In Step 304, the response of the chemical transducer in the reference region to the excitation light in presence of the reference concentration of the species of interest, i.e., the reference response, is measured. The measurement may be, for example, an intensity of light re-emitted by the chemical transducer in the reference region in response to the exposure to the excitation light, or it may be a time constant describing the time course of the re-emission of light after the excitation light was provided. The measurement may be obtained by the detector unit, and may be provided, for example, as a voltage, a current, or a digital signal.

In Step 306, a reference function that defines a relationship between the known, defined reference concentration of the species of interest and the reference island detector unit signal is identified. The reference function may be a gain factor that may be applied to the reference island detector unit signal to calculate the reference concentration of the species of interest.

In Step 308, the chemical transducer in the sensor region is exposed to a calibration analyte that contains a calibration concentration of the species of interest. The calibration concentration may be known and defined. The chemical transducer in the sensor region may be exposed to the calibration analyte, for example, by immersing the sensor region (e.g., a sensor island on a substrate, as shown in FIGS. 1 and 2) into a liquid reference analyte, or by placing it into a chamber that contains a gaseous reference analyte. The calibration concentration of the species of interest may be chosen to approximately match the concentrations of the species of interest to be measured by the optode sensor with integrated reference. For example, a calibration analyte with a 0% calibration concentration of the species of interest may be chosen if the optode sensor with integrated reference is intended to measure analytes that contain low concentration of the species of interest. Further, Step 308 may be repeated for multiple calibration analytes with different calibration concentrations in order to obtain the sensor characteristics for a range of concentrations of the species of interest.

In Step 310, the chemical transducer in the sensor region is exposed to excitation light. The excitation light may be provided by the exciter unit of the detecting device. The duration of the exposure to the excitation light may vary, for example the exposure may be pulsed, or it may be continuous. The characteristics of the light (including intensity, wavelength, and duration of exposure) may be selected such that the chemical transducer may, in response, re-emit light, for example via fluorescence or phosphorescence, as previously described. In one embodiment of the invention, the characteristics of the excitation light applied to the chemical transducer of the sensor region are substantially similar to the characteristics of the excitation light applied to the chemical transducer of the reference region. Step 310 may be repeated if multiple calibration analytes with different calibration concentrations are measured.

In Step 312, the response of the chemical transducer in the sensor region to the excitation light in presence of the calibration concentration of the species of interest, i.e., the sensor region response under calibration conditions, is measured. The measurement may be, for example, an intensity of light re-emitted by the chemical transducer in the sensor region in response to the exposure to the excitation light, or it may be a time constant describing the time course of the re-emission of light after the excitation light was provided. The measurement may be obtained by the detector unit, and may be provided, for example, as a voltage, a current, or a digital signal. Step 312 may be repeated if multiple calibration analytes with different calibration concentrations are measured.

In Step 314, a sensor function that defines a relationship between the known, defined calibration concentration of the species of interest in the calibration analyte and the sensor island detector unit signal is identified. The sensor function may be a gain factor that may be applied to the sensor island detector unit signal to calculate an uncompensated concentration of a species of interest, i.e., a concentration that is not adjusted for aging effects of the chemical transducer. If multiple calibration analytes with different calibration concentrations are measured, the sensor function may be a relationship, that may include an offset component and a gain component, or it may be any other type of linear or non-linear relationship that may be represented for example by mathematical functions or lookup tables.

FIG. 4 shows a method for measuring a species of interest in an analyte. The measurement unit used to quantify the species of interest in the analyte may be concentration. Alternative units may include, but are not limited to, saturation, partial saturation, and partial pressure. The method for measuring a species of interest in an analyte includes steps to compensate for aging (i.e., photo-bleaching) of the chemical transducers employed for sensing the species of interest. Photo-bleaching is a photochemical alteration of the chemical transducer which may, over time, reduce the light re-emission response by the chemical transducer in response to excitation light. Because the measurements of the species of interest in the analyte is based on measurements of light re-emitted by a chemical transducer that is exposed to the species of interest, the accuracy of uncompensated measurements may be negatively affected by photo-bleaching, or aging in general. The compensation for aging, in accordance with one or more embodiments of the invention, is based on a measurement of a reference environment which contains a known reference concentration of the species of interest in addition to the measurement of the analyte which contains an unknown concentration of the species of interest. Because the reference concentration of the species of interest in the reference environment is known, a correction of the measurement obtained from the reference detector unit signal may be performed to match the known reference concentration. In one or more embodiments of the invention, the same type of chemical transducer is used for measuring the reference environment and the analyte, thus allowing to also apply the correction to adjust the measurement obtained from the sensor detector unit signal. Accordingly, the concentration of the species of interest, after applying the correction, may not be affected by aging of the chemical transducers. If different chemical transducers, where aging may differently affect the measurements of the reference environment and the analyte, are used, the differences may be understood, thus enabling appropriate compensation, despite differing aging behaviors of the chemical transducers.

Turning to FIG. 4, in Step 400, the chemical transducer in the reference region is exposed to the reference environment that contains a reference concentration of the species of interest.

In Step 402, the chemical transducer in the reference region is exposed to excitation light. The excitation light may be provided by the exciter unit of the detecting device. The duration of the exposure to the excitation light may vary, for example the exposure may be pulsed, or it may be continuous. The characteristics of the excitation light (including intensity, wavelength and duration of exposure) may be selected such that the chemical transducer may, in response, re-emit light, for example via fluorescence or phosphorescence, as previously described.

In Step 404, the response of the chemical transducer in the reference region to the excitation light in presence of the reference concentration of the species of interest, is measured. The measurement may be a value for the reference concentration of the species of interest, based on the output of the reference detector unit. Because aging may have affected the chemical transducer, the reference concentration value may deviate from the known, fixed reference concentration of the reference environment. The measurement may be based on an intensity of light re-emitted by the chemical transducer in the reference region in response to the exposure to the excitation light, or on a time constant describing the time course of the re-emission of light after the excitation light was provided. The measurement may be obtained by multiplying the output of the reference detector unit (which may be, for example, a voltage, a current, or a digital signal) with the reference function previously obtained in Step 306.

In Step 406, a compensation for the aging of the chemical transducer is determined. The compensation may be determined based on the discrepancy between the response of the chemical transducer measured in Step 404 and the reference response of the chemical transducer, originally obtained during the calibration of the optode sensor with integrated reference in Step 304, for example during manufacturing of the optode sensor. A discrepancy may exist when aging (e.g. photo-bleaching) has affected the chemical transducer. As a chemical transducer ages, the intensity of the re-emitted light may decrease, and/or the time constant of the response may become shorter, i.e., the intensity of the re-emitted light may decay more rapidly. A compensation may be obtained additively (offset compensation) or multiplicatively (gain compensation). For example, if a hypothetical time constant describing the time-course of the re-emitted light drops from originally 10 ms to 5 ms, the compensation may be performed additively by adding 5 ms to the measured time constant, or it may be performed multiplicatively by applying a factor "2", to compensate for the effect of aging of the chemical transducer, thereby restoring the original response, as obtained during the calibration described in FIG. 3. Whether an addition or a multiplication is performed may depend on whether photo-bleaching in a particular chemical transducer primarily affects the response (e.g. the intensity of the re-emitted light, or the time-course of the re-emission of light) of the chemical transducer in an additive or in a multiplicative manner. If, for example, the difference between the reference concentration of the species of interest and the concentration of the species of interest in the analyte is relatively small, an additive compensation may be relatively accurate. If, in contrast, the difference between the reference concentration of the species of interest and the concentration of the species of interest in the analyte is larger, a compensation that includes an offset and a gain component (i.e., a compensation that corrects the measured response additively and multiplicatively) may provide more accurate results. Such a compensation may be performed, for example, using two reference islands with different reference concentrations of the species of interest, e.g. one low concentration and one high concentration of the species of interest. Curve fitting may be applied to the concentration measurements obtained from the two reference islands, for example using a linear model that includes offset and gain components. The measured concentration of the species of interest in the analyte may then be corrected additively and multiplicatively by applying the linear model. Further, any other type of linear or non-linear relationships that may be expressed, for example, as mathematical functions or in lookup tables may be used as a compensation for the aging of the chemical transducer.

In Step 408, the chemical transducer in the sensor region is exposed to the analyte to be measured, i.e., the analyte that contains an unknown concentration of the species of interest. The chemical transducer in the sensor region may be exposed to the analyte, for example, by immersing the sensor region (e.g., the sensor island on the substrate, as shown in FIGS. 1 and 2) into a liquid analyte, or by placing it into a chamber that contains a gaseous analyte.

In Step 410, the chemical transducer in the sensor region is exposed to excitation light. The excitation light may be provided by the exciter unit of the detecting device. The duration of the exposure to the excitation light may vary, for example the exposure may be pulsed, or it may be continuous. In one embodiment of the invention, the characteristics of the excitation light applied to the chemical transducer of the sensor region are substantially similar to the characteristics of the excitation light applied to the chemical transducer of the reference region.

In Step 412, the response of the chemical transducer in the sensor region to the excitation light in presence of the unknown concentration of the species of interest in the analyte, is measured. The measurement may be a value for the concentration of the species of interest in the analyte, based on the output of the sensor detector unit. Because aging may have affected the chemical transducer, the obtained concentration value may be inaccurate, i.e., the measurement is an uncompensated measurement. The uncompensated measurement may be based on an intensity of light re-emitted by the chemical transducer in the sensor region in response to the exposure to the excitation light, or on a time constant describing the time course of the re-emission of light after the excitation light was provided. The uncompensated measurement may be obtained by multiplying the output of the sensor detector unit (which may be, for example, a voltage, a current, or a digital signal) with the sensor function previously obtained in Step 314.

In Step 414, the uncompensated measurement of the species of interest, obtained in Step 412 is corrected for the aging of the chemical transducer by applying the compensation, obtained in Step 406, to the uncompensated measurement. The compensated measurement of the species of interest may be independent from the aging of the chemical transducer and may therefore provide an accurate estimate of the actual concentration of the species of interest in the analyte. As previously discussed, the compensation may be performed by applying an offset correction, a gain correction, or it may perform both an offset and a gain correction. Further, the compensation may rely on any other linear and/or non-linear relationships, identified in Step 406.

Embodiments of the invention may enable an optode sensor with integrated reference to accurately estimate a concentration of a species of interest in an analyte, despite aging of the chemical transducer used for measuring the species of interest, even though aging affects the characteristics of the chemical transducer. Further, because the chemical transducers in the sensor region and in the reference region are exposed to similar environmental conditions, the chemical transducers and the measurements obtained from the chemical transducers may be equally affected by these environmental conditions (e.g. temperature), thereby enabling cancellation of these effects. The optode sensor with integrated reference, in accordance with one or more embodiments of the invention, may provide accurate concentration measurements without requiring repeated calibration. An initial identification of the characteristics of the optode sensor with integrated reference may be sufficient to enable accurate estimation of presence and/or concentration of species of interest for the lifetime of the sensor. The optode sensor with integrated reference may therefore be used in applications that prohibit repeated calibration and/or access to the sensor. The initial calibration further allows the detection of and compensation for intended and or unintended deviations. Such deviations may include optical misalignment of components, deviating detector sensitivities, deviating exciter unit intensities, deviating responsiveness of the chemical transducers, etc. In one embodiment of the invention, measurements obtained from the reference region of the sensor may be used to assess aging and expected remaining lifetime of the sensor with the integrated reference. For example, replacement of the sensor may be considered when the measured response of the chemical transducer in the reference region has dropped by 80%, in comparison to the originally obtained response.

Figure 5:
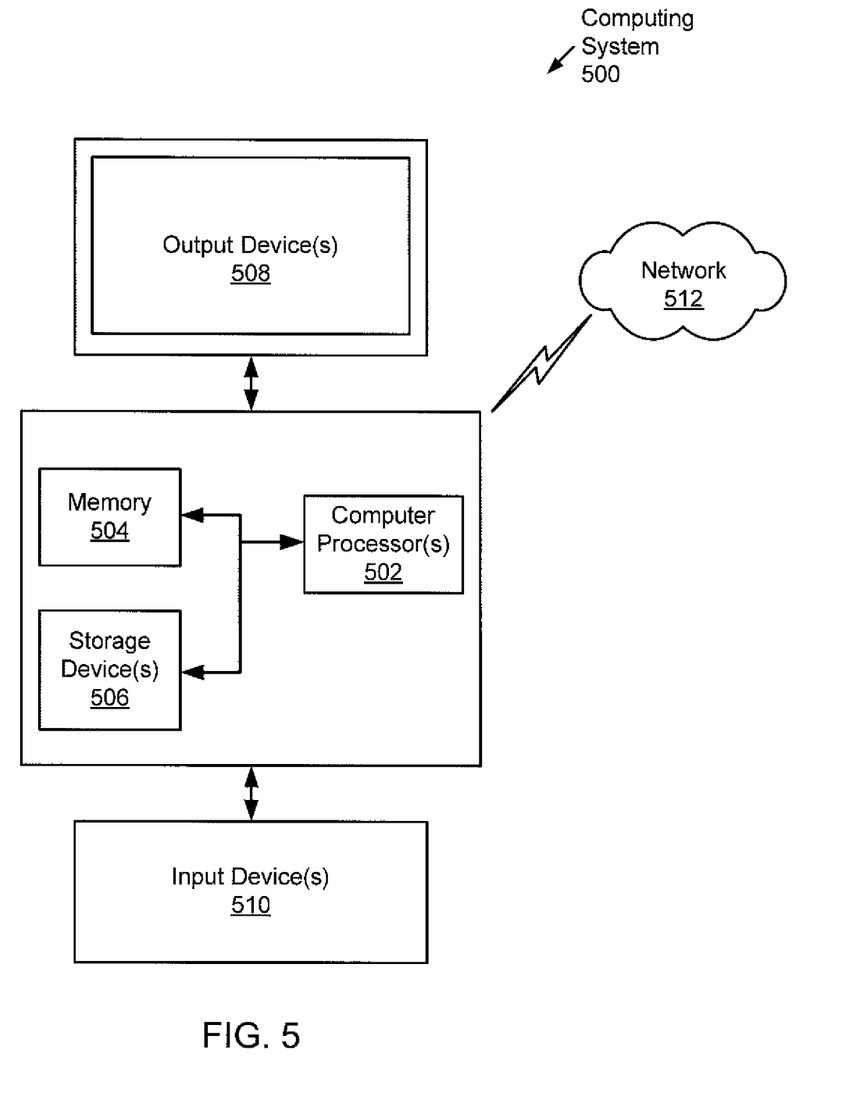
FIG. 5 shows a computer system in accordance with one or more embodiments of the invention.

Embodiments of the invention may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention. For example, as shown in FIG. 5, the computing system (500) may include one or more computer processor(s) (502), associated memory (504) (e.g., random access memory (RAM), cache memory, flash memory, etc.), one or more storage device(s) (506) (e.g., a hard disk, an optical drive such as a compact disk (CD) drive or digital versatile disk (DVD) drive, a flash memory stick, etc.), and numerous other elements and functionalities. The computer processor(s) (502) may be an integrated circuit for processing instructions. For example, the computer processor(s) may be one or more cores, or micro-cores of a processor. The computing system (500) may also include one or more input device(s) (510), such as a touchscreen, keyboard, mouse, microphone, touchpad, electronic pen, or any other type of input device. Further, the computing system (500) may include one or more output device(s) (508), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (500) may be connected to a network (512) (e.g., a local area network (LAN), a wide area network (WAN) such as the Internet, mobile network, or any other type of network) via a network interface connection (not shown). The input and output device(s) may be locally or remotely (e.g., via the network (512)) connected to the computer processor(s) (502), memory (504), and storage device(s) (506). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (500) may be located at a remote location and connected to the other elements over a network (512). Further, one or more embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system for obtaining a measurement of a species of interest in an analyte, the system comprising:
at least one reference region comprising a first chemical transducer different from the species of interest,
wherein the first chemical transducer is permanently present in the at least one reference region;
wherein the at least one reference region is exposed to at least one reference environment comprising at least one reference concentration of the species of interest, and
wherein at least one optical response of the first chemical transducer depends on the at least one reference concentration of the species of interest in the at least one reference region;
a sensor region comprising a second chemical transducer different from the species of interest,
wherein the second chemical transducer is permanent present in the sensor region;
wherein the sensor region is exposed to the analyte, and
wherein an optical response of the second chemical transducer depends on a concentration of the species of interest in the analyte in the sensor region;
an exciter unit
for exposing the first chemical transducer in the at least one reference region to an excitation light while the first chemical transducer in the at least one reference region is exposed to the at least one reference environment, and
for exposing the second chemical transducer in the sensor region to the excitation light while the second chemical transducer in the sensor region is exposed to the analyte;
a detector unit
for obtaining a measurement of the at least one optical response of the first chemical transducer in the at least one reference region to the excitation light, and
for obtaining a measurement of the optical response of the second chemical transducer in the sensor region to the excitation light; and
a processing unit for determining a compensation for aging of the first chemical transducer in the at least one reference region from a discrepancy between the measurement of the at least one optical response of the first chemical transducer to the excitation light and at least one optical reference response of the first chemical transducer, and for obtaining the measurement of the species of interest in the analyte by applying the compensation for aging of the first chemical transducer to the measurement of the optical response of the second chemical transducer.

2. The system of claim 1, wherein the at least one reference region and the at least one reference environment is enclosed by an encapsulation, and wherein the encapsulation is impermeable to the species of interest.

3. The system of claim 1, wherein the at least one reference region and the sensor region are separately located on a surface of a substrate that is impermeable to the species of interest.

4. The system of claim 1, wherein the exciter unit comprises at least one selected from the group consisting of an LED, a laser, an incandescent light bulb, a fluorescent light bulb and a high-intensity discharge light bulb.

5. The system of claim 1, wherein the detector unit comprises at least one selected from the group consisting of a photodiode, a phototransistor, a photoresistor, a CCD array, and a CMOS array.

6. The system of claim 1, wherein the first and the second chemical transducers are porphyrin-based.

7. The system of claim 1, wherein the first and the second chemical transducers are identical chemical transducers.

8. The system of claim 1, wherein the aging of the first and the second chemical transducers is caused by photo-bleaching.

9. The system of claim 1, wherein the exposure of the first chemical transducer to the excitation light and the exposure of the second chemical transducer to the excitation light are substantially the same.

10. The system of claim 1, wherein the optical responses of the first and the second chemical transducers are one selected from the group consisting of an intensity of a re-emitted light and a time course of the intensity of tin re-emitted light.

11. The system of claim 10, wherein the re-emitted light is generated by one selected from the group consisting of fluorescence and phosphorescence.

12. A method for obtaining a measurement of a species of interest in an analyte using an optode sensor, the method comprising:

exposing at least one reference region comprising a first chemical transducer, different from the species of interest, to at least one reference environment comprising at least one reference concentration of the species of interest,
  wherein the first chemical transducer is permanently present in the at least one reference region, and
  wherein at least one optical response of the first chemical transducer depends on the at least one reference concentration of the species of interest in the at least one reference region;
exposing the first chemical transducer in the at least one reference region to excitation light;
obtaining a measurement of the at least one optical response of the first chemical transducer in the at least one reference region to the excitation light during the exposure to the at least one reference environment;

determining a compensation for aging of the first chemical transducer from a discrepancy between the measurement of the at least one optical response of the first chemical transducer in the at least one reference region to the excitation light and at least one optical reference response of the first chemical transducer;
exposing a sensor region comprising a second chemical transducer, different from the species of interest, to the analyte,
  wherein the second chemical transducer is permanently present in the sensor region, and
  wherein an optical response of the second chemical transducer depends on a concentration of the species of interest in the analyte in the sensor region;
exposing the second chemical transducer in the sensor region to excitation light;
obtaining a measurement of the optical response of the second chemical transducer in the sensor region to the excitation light during the exposure to the analyte;
obtaining the measurement of the species of interest in the analyte by applying the compensation for aging of the first chemical transducer to the measurement of the optical response of the and chemical transducer to the excitation light during the exposure to the analyte.

13. The method of claim 12, wherein the measurement of the species of interest in the analyte is one selected from the group consisting of a concentration, a relative saturation, and a partial pressure.

14. The method of claim 12, wherein the first and the second chemical transducers are identical chemical transducers.

15. The method of claim 12, wherein the exposure of the first chemical transducer to the excitation light and the exposure of the second chemical transducer to the excitation light are substantially the same.

16. The method of claim 12, wherein the optical responses of the first and the second chemical transducers are one selected from the group consisting of an intensity of a re-emitted light and a time course of the intensity of the re-emitted light.

17. The method of claim 16, wherein the re-emitted light is generated by one selected from the group consisting of fluorescence and phosphorescence.

18. The method of claim 12, wherein a first temperature of the at least one reference region and a second temperature of the sensor region are substantially the same, during the obtaining of the measurement of the at least one optical response of the first chemical transducer and during the obtaining of the measurement of the optical response of the second chemical transducer.

19. The method of claim 12, wherein the compensation for aging of the first chemical transducer is one selected from the group consisting, of a linear relationship and a nonlinear relationship.

20. The method of claim 12, further comprising an initially performed calibration, the initially performed calibration comprising:

exposing the at least one reference region comprising the first chemical transducer to the at least one reference environment;
exposing the chemical transducer in the at least one reference region to the excitation light;
obtaining the at least one optical reference response of the first chemical transducer by measuring at least one original optical response of the first chemical transducer in the at least one reference region to the excitation light during the exposure to the at least one reference environment.

\* \* \* \* \*